(12) United States Patent
Chan et al.

(10) Patent No.: US 7,829,098 B2
(45) Date of Patent: Nov. 9, 2010

(54) HERBAL POWDER EXTRACTS AND METHODS OF PREPARING AND USING THE SAME

(75) Inventors: Helen Hei Ling Chan, Hong Kong (HK); Clara Bik San Lau, Kowloon (HK); Moses Sing Sum Chow, Tai Po (HK)

(73) Assignee: Vita Green Health Products Co., Ltd, Hong Kong SAR (CN)

( * ) Notice: Subject to any disclaimer, the term of this patent is extended or adjusted under 35 U.S.C. 154(b) by 480 days.

(21) Appl. No.: 11/269,294

(22) Filed: Nov. 8, 2005

(65) Prior Publication Data

US 2007/0104727 A1 May 10, 2007

(51) Int. Cl.
*A61K 36/09* (2006.01)
*A61K 9/00* (2006.01)
*A61K 47/00* (2006.01)

(52) U.S. Cl. .................... 424/195.15; 424/400; 424/439

(58) Field of Classification Search ........................ None
See application file for complete search history.

(56) References Cited

U.S. PATENT DOCUMENTS

| | | | |
|---|---|---|---|
| 4,140,578 A | 2/1979 | Yoshikumi et al. | |
| 4,229,570 A | 10/1980 | Ueno et al. | |
| 4,614,733 A | 9/1986 | Yoshikumi et al. | |
| 4,851,395 A | 7/1989 | Ueno et al. | 514/54 |
| 4,975,422 A | 12/1990 | Kanoh et al. | 514/54 |
| 5,824,648 A * | 10/1998 | Yang et al. | 514/14 |
| 6,511,683 B1 * | 1/2003 | Gahler et al. | 424/737 |
| 6,746,675 B2 | 6/2004 | Goino | 424/195.15 |
| 2004/0137127 A1 * | 7/2004 | Khare | 426/590 |
| 2005/0233011 A1 * | 10/2005 | Beavers | 424/725 |
| 2006/0057157 A1 * | 3/2006 | Mahajna et al. | 424/195.15 |

FOREIGN PATENT DOCUMENTS

| | | |
|---|---|---|
| EP | 1918383 A1 | 5/2008 |
| JP | 2000-336025 A | 12/2000 |
| KR | 1993-0003311 B1 | 4/1993 |
| SU | 961565 A | 9/1982 |

OTHER PUBLICATIONS

C.B.S. Lau et al., "Cytotoxic activities of *Coriolus versicolor* (Yunzhi) extract on human leukemia and lymphoma cells by induction of apoptosis," Life Sciences 75:797-808 (2004).
Jian Cui and Yusuf Chisti, "Polysaccharopeptides of *Coriolus versicolor*: physiological activity, uses, and production," Biotechnology Advances 21:109-122 (2003).
Hsieh TC, Wu JM, "Cell growth and gene modulatory activities of Yunzhi (Windsor Wunxi) from mushroom Trametes versicolor in androgen-dependent and androgen-insensitive human prostate cancer cells," Int. J. Oncol. 18(1):81-8 (Jan. 2001).
International Search Report and Written Opinion issued Jun. 20, 2007 by the International Searching Authority in corresponding PCT International Application No. PCT/US06/43170.
Koch et al, The Influence of Selected Higher Basidiomycetes on the Binding of Lipopolysaccharide to CD14+ Cells and on the Release of Cytokines, International Journal of Medicinal Mushrooms, 2002, pp. 229-235, vol. 4(3).
Ho et al, Differential Anti-tumor Activity of *Coriolus versicolor* (Yunzhi) Extract through p53- and/or Bcl-2-Dependent Apoptotic Pathway in Human Breast Cancer Cells, Cancer Biology & Therapy, 2005, pp. e11-e17, vol. 4(6).

\* cited by examiner

*Primary Examiner*—Christopher R Tate
*Assistant Examiner*—Randall Winston
(74) *Attorney, Agent, or Firm*—Eagle IP Limited; Jacqueline C. Lui

(57) ABSTRACT

Methods for preparing an herbal powder extract from a polysaccharide-peptide rich mushroom, including *Coriolus versicolor* (Yunzhi), are disclosed. A more effective, highly pure Yunzhi powder extract, methods of preparing and using the same in ameliorating cancerous cell proliferations and hepatitis and are also disclosed.

7 Claims, 8 Drawing Sheets

HERBAL POWDER EXTRACTS AND METHODS OF PREPARING AND USING THE SAME

FIELD OF INVENTION

The present invention relates to herbal powder extracts that contain *Coriolus versicolor* (Yunzhi) powder for prophylaxis or adjuvant therapy or treatment of cancers and hepatitis. The present invention also relates to methods of preparing and using a polysaccharide-peptide rich mushroom powder extract including Yunzhi.

BACKGROUND OF INVENTION

Yunzhi, also known as *Coriolus versicolor* or cloud mushroom, is an edible fungus that belongs to the order Polystrictus, Polyporales, and Basidomycetes of the mushroom genus. It is considered a medicinal mushroom and use in Traditional Chinese Medicine.

Yunzhi contains active ingredient polysaccharides that has been shown to enhance immune function, increase immunocyte's quantity, swallow and kill tumor cells, increase white blood cell count. It has also been used to treat chronic, persistent and active hepatitis, b-type hepatitis with the general effective ratio of 82.4%. Its effective rate in treating chronic bronchitis reaches 85%. With anti-aging and health maintaining function, it can clear free radicals, stimulate drug effects, invigorate kidney and strengthen liver.

Since the effectiveness of Yunzhi in boosting immune system function was discovered in 1943, there has been a demand for a supply of Yunzhi polysaccharides. It is important to know that not all the Yunzhi extracts are the same in terms of the polysaccharide content. It is an objective of the present invention to provide a better method for preparing a Yunzhi formulation that is more effective and contain highly pure Yunzhi powder extract.

SUMMARY OF THE INVENTION

The present invention pertains to methods for preparing a polysaccharide-peptide rich mushroom powder extract. The methods include providing a polysaccharide-peptide rich mushroom, having the mushroom crushed and extracted by alkanol and an aqueous solvent, filtering and concentrating the extracts and spray-drying the concentrate to obtain a polysaccharide-peptide rich mushroom powder extract. The alkanol may be ethanol or an ethanol:water mixture. The aqueous solvent may be water.

The present invention also pertains to methods for making a *Coriolus versicolor* (Yunzhi) powder extract. The methods include providing Yunzhi raw material, having the raw material crushed and extracted by a solvent, filtering and concentrating the extract and spray-drying the concentrate to form a Yunzhi powder extract.

In preferred embodiment, the methods of the invention are performed by four times extractions: twice with 50% ethanol and twice with water. In another preferred embodiment, the methods of the invention are performed under the condition that the weight versus volume ratio of the herbal material and the solvent is preferred to be about 1:5, 1:2~3 for the first and second extractions, 1:2~3 and 1:1~3 for the third and fourth extractions, respectively.

In another aspect, the present invention is directed to a herbal powder extract that contains *Coriolus versicolor* (Yunzhi) powder prepared by the methods of the invention. In one embodiment, the herbal powder extract of the invention features a chemical profiling described infra. The instant disclosed herbal powder extracts contain Yunzhi powder that is more effective in anti-proliferation of cancer cells than that made by other old methods.

The herbal powder extract of the present invention can additionally contain a pharmaceutically acceptable excipient and/or carrier and be formulated into various dosage forms, such as granules, capsules, tablets, powders, and bolus, for orally administration. The preferred formulation is capsule.

The herbal powder extract of the present invention has potential therapeutic effects on diseases that can be alleviated by stimulating or modulating the immune system of the body and can be used for prevention and/or treatment of hepatitis and cancers including breast cancers and leukemia. The herbal pharmaceutical composition can be safely used by patients at any ages and physical conditions, including the weak, the elderly, and the debilitated.

DETAILED DESCRIPTION

Figure 1:
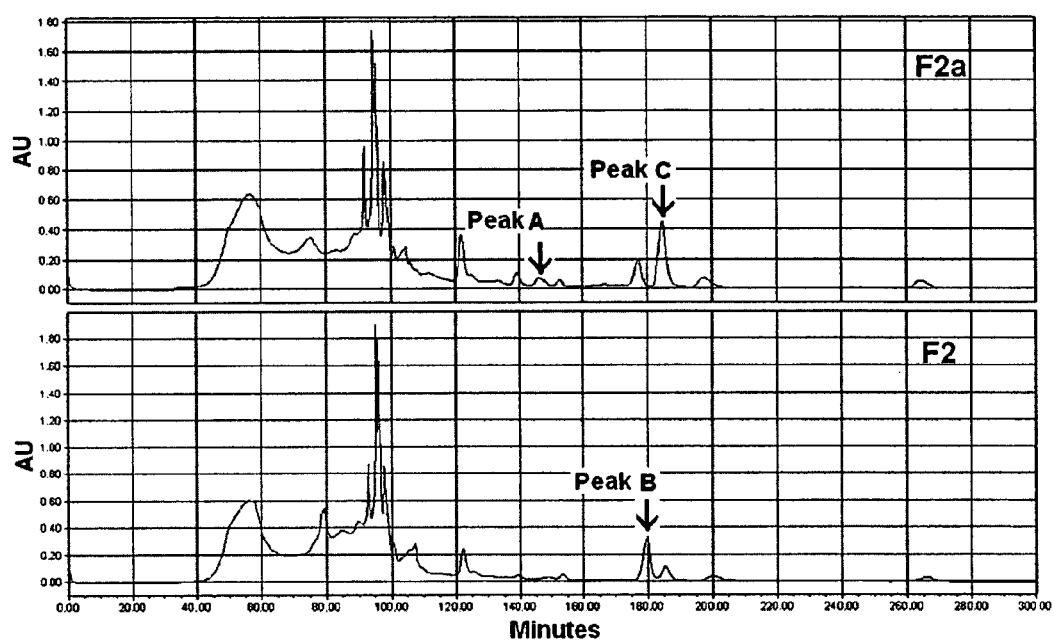
FIG. 1 shows HPLC (high performance liquid chromatography) profiles of Yunzhi powder extracts F2a and F2 at UV 265 nm.

The present invention provides methods for preparing a polysaccharide-peptide rich mushroom powder extract. The methods include (a) providing a polysaccharide-peptide rich mushroom and crushing the mushroom into coarse powder; (b) extracting the mushroom coarse powder with alkanol to obtain an alkanol extract and filtering the alkanol extract to obtain an alkanol filtrate; (c) extracting the residue from step (b) with an aqueous solvent to obtain an aqueous extract and filtering the aqueous extract to obtain an aqueous filtrate; (d) combining and concentrating the above filtrates to obtain a concentrate; and (e) spray-drying the concentrate to form the polysaccharide-peptide rich mushroom powder extract.

The present invention also provides methods for preparing a *Coriolus versicolor* (Yunzhi) powder extract. The methods include (a) providing Yunzhi raw material and crushing the raw material into coarse powder; (b) extracting the coarse powder with a solvent to obtain a liquid extract; (c) filtering the liquid extract to obtain a filtrate; (d) concentrating the filtrate to obtain a concentrate; and (e) spray-drying the concentrate to form the Yunzhi powder extract.

In preferred embodiments, the methods of the invention use 50% ethanol in water (v/v) as a solvent for extraction. Also in preferred embodiments, the ethanol or water extraction step is performed more than once. In certain preferred embodiments, the extraction step is performed four times and the solvent used is 50% ethanol for the first and second extractions, water for the third and fourth extractions.

A Yunzhi powder extract prepared according to the methods of the invention are highly purified and more effective in inhibiting the growth of cancer cells. A Yunzhi powder extract prepared according to the methods of the invention is useful for preventing and treating hepatitis and inhibiting growth of cancer cells including leukemia and breast carcinoma.

The alkanol may be an alkanol in the range of a C1-C12 alkanol, C1-C10 alkanol, a C1-C8 alkanol, a C1-C6 alkanol, a C1-C4 alkanol, a C1-C3 alkanol, a C2-C12 alkanol, a C2-C10 alkanol, a C2-C9 alkanol, a C2-C8 alkanol, a C2-C7 alkanol, a C2-C6 alkanol, a C2-C5 alkanol, a C2-C4 alkanol or a C2-C3 alkanol, or a mixture thereof. The alkanol may be a C2, C3, C4, C5, C6, C7, C8, C9, C10, C11, or C12 alkanol. The alkanol may be used by itself or as an aqueous mixture. For example, a 99:1 to 20:80 alkanol:water wt/wt or vol/vol or wt/vol or vol/wt mixture may be used. An alkanol:water mixture in the range of 10:90 to 90:10 (volume/volume), 20:80 to 80:20 (volume/volume), 30:70 to 70:30 (volume/volume), 40:60 to 60:40 (volume/volume) or 45:55 to 55:45 (volume/volume) may be used as a solvent for extraction. Throughout the specification and claims the term "alkanol" is to be taken as including an alkanol by itself or an alkanol:water mixture.

Yunzhi Pure Powder and Formulations

Yunzhi pure powder extract and formulations of the present invention are prepared by the following procedures:

(1) Preparation of Coarse Powders

Yunzhi raw herbs *Coriolus versicolor* L. of Polyporaceae family, collected in Guangxi, Yunnan and Guizhou provinces of China, also called *Polysticus versicolor*, are crushed into coarse powder, which is then used for preparation of extracts. Natural Yunzhi is preferred, although cultivated Yunzhi may be used for extraction.

(2) Preparation of Extracts

Yunzhi coarse powders are repeatedly extracted by solvents. Ethanol, preferred 50% in water (v/v), is used for the first and the second extraction, and purified water is used for the third and the fourth extraction. The preferred weight versus volume ratios of coarse powder and the solvent are about 1:5, 1:2~3, 1:2~3 and 1:1~3 for the first, second, third and fourth extraction, respectively. The time for each extraction is preferred to be 1.5~2 hours. The extracts are filtered and the filtrates are combined, concentrated and made into pure powder, as described below.

(3) Concentration of Extracts

The filtrate obtained from above (2) is concentrated by evaporation under vacuum and at about 50~85° C. until a concentrate with an optimal relative density of 1.05~1.12, preferably around 1.05~1.08, is obtained.

(4) Preparation of Pure Powder

The concentrate described in (3), is further spray-dried to form pure powder. The concentrate is preheated to a temperature of about 60~70° C. before being injected into the cabinet of the spray dryer. The incoming temperature of the spray dryer cabinet is adjusted to an optimal temperature. The optimal temperature is defined as the temperature at which the highest yield of total polysaccharides in the final powder products can be obtained. The range of the optimal temperature for incoming air is about 150~250° C., preferred at 200~230° C., more preferred at 150~170° C. The outgoing temperature is preferred to be at 70~100° C. The preferred range of the temperature for the highest yield of total polysaccharides in the final powder products may vary according to the individual spray dryer used. The dry powder is then passed through a sieve with a mesh size of about 80 to ensure that the size of the dry powder grains is within an acceptable range.

(5) Preparation of Pharmaceutical Formulations

The Yunzhi pure powder can be processed into tablets, bolus, powders, capsules, and granules by means of formulation which are well-known to those of ordinary skill in the art, particularly in the pharmaceutical industry. Excipients, binders, carriers, fillers may be added to the pure powder to form various dosage forms if necessary.

The following examples are for illustrative purpose and are not intended to limit the scope of the invention. Reasonable variations, such as those understood by reasonable artisans, can be made without departing from the scope of the present invention.

EXAMPLE

Preparation of Yunzhi Powder Extract F2 and F2a

According to one embodiment of the present invention, Yunzhi pure powder named F2 and F2a were prepared as following steps. The difference in manufacturing F2 and F2a lies in how they were dried. F2 was dried by spray-drying process. F2a was dried by vacuum-drying process.

Raw Materials

Yunzhi raw herb (*Coriolus versicolor*, also called *Polysticus versicolor*) was obtained from the Tien Lin County Agriculture Department, China, which is the fruiting bodies of *Coriolus versicolor* growing wild in the Tien Lin County of Guangxi province of mainland China. The Yunzhi raw herb was collected in September and October (Autumn). The *Coriolus versicolor* was authenticated by Professor Zhan Xiao-qing (Mycology expert, Institute of Microbiology Chinese Academy of Sciences, Beijing, China). Herbarium voucher specimen (No. 2003-2510) was deposited at the museum of the Institute of Chinese Medicine, the Chinese University of Hong Kong.

The fruiting bodies were cleaned, crushed in the pretreatment process. The cut material, or Yunzhi coarse powder, obtained from the pretreatment was then extracted with 50% ethanol. For every 28 Kg production batch of finished products, it required about 350 Kg of Yunzhi coarse powder and 2450 liters of 50% ethanol. The pretreatment and extraction steps are described below:

Pretreatment

Yunzhi raw herb was first pretreated by concoction and crushing to obtain Yunzhi cut material or Yunzhi coarse powder as described below.

1. Concoction

Yunzhi raw herb was quickly rinsed with running tap water to remove silt and impurities and then steamed in a stainless steel steamer for one hour to kill potential plant parasites and eggs, and dried by air or in oven at 60° C.

2. Crushing 367.5 Kg of Yunzhi raw herb was crushed into powder by pressing it through a mill (Hammer Type Grinder, Model No. 9FQ37-18) with a sieve of mesh size of 12 mm to obtain the cut plant material, or coarse powder, of the size below or around 12 mm. The coarse powder was collected and kept in a tightly closed plastic container. Each container was labeled with the material's name, batch number, date and weight, and placed in a designated place for storage at a temperature of around 0°~30° C. and moisture of about 60~75%.

Extraction

Yunzhi coarse powder was repeatedly extracted with 50% ethanol as follows:

1. First Extraction

Approximate 350 Kg of Yunzhi coarse powder was first extracted with 1750 liters of 50% ethanol:50% water (v/v) alternatively referred to as 50% ethanol. Two layers. of gauze lined the bottom of the percolator and sufficient amount of 50% ethanol was added through a solvent delivery hole to displace the air at the bottom. About ⅓ of the Yunzhi coarse powder was added and evenly distributed. Approximately 875 liters of 50% ethanol was added and the content of the percolator was pressed flat. The remaining ⅔ of the Yunzhi coarse powder was added and the material delivery hole was closed and sealed tightly. Another 875 liter of 50% ethanol was added. A circulation pump was turned on for 10 minutes and the mixture was soaked for over 12 hours before proceeding to steam extraction. The circulation pump was connected to the percolator, allowing the extract at the bottom of the percolator to circulate back to the top of the percolator.

To perform steam extraction, water steam was directed into the steam layer of the percolator. The water steam pressure was controlled at 0.1~0.2 MPa via manual steam valves located on the percolator's steam layer. The circulation pump was turned on once every 10 minutes, for 10 minutes each time during this peroid.

As water steam entered the percolator's steam layer, the solvent was heated, the vapor rose, cooled, condensed, and fell down to the bottom of the percolator. This recycling process is called solvent reflux. A vapor recycling tube connected to the top of percolator was in close contact with a condenser and a cooler at two separate portions, allowing solvent reflux to occur. The entrance valves of cooler and condenser were opened when the temperature of the extract rose to near the boiling point of the solvent, around 70° C. in the case of 50% ethanol. Water flowed into the cooler and condenser.

The time needed for solvent reflux to occur depended on the amount of solvents, steam pressure and boiling points of the solvents. Based on the amount of input plant materials used here, the time needed for solvent reflux was about 30 minutes for ethanol extraction and about 1 hour for water extraction.

Once the solvent reflux started, the time was noted and recorded. The temperature at which the state of solvent reflux could be maintained is a "fixed temperature" that was used for simmering the mixture. The mixture was simmered at a fixed temperature for about 2 hours, while the inside pressure of the percolator was maintained at around 0.02~0.05 MPa via the steam valves. When 50% ethanol is used for extraction, the fixed temperature was at about 80° C. and when water was used, the fixed temperature was at about 90~95° C. The extract was distributed via the circulation pump once every 10~15 minutes, preferably once every 15 minutes, and for 5 minutes each time during this period. This allowed the liquid extract to circulate periodically so that herbal materials could be fully extracted.

The extract was filtered according to standard operating procedures. In practice, the extract left the percolator, passed through a filter and the filtrate entered a storage container via the circulation pump.

2. Second Extraction

The residue obtained from the above first extraction was further extracted with approximate 700 liters of 50% ethanol as the second extraction according to the method described above. The filtrate from the second extraction was combined with that of the first extraction.

3. Third and Fourth Extraction

The residue from the second extraction was extracted twice more with 700 liters and 350 liters of purified water as the third and the fourth extractions, respectively. The water extraction was performed with circulation according to the methods described above, except that the periods of the extraction under circulation were 2 hours and 1.5 hours for the third and fourth extraction, respectively.

Concentration

The filtrates obtained from the above extractions were combined and then went through the process of ethanol recovery and concentration.

1. Ethanol Recovering

Ethanol was recovered from the filtrates at a vacuum of about −0.07 Mpa and at a vapor pressure of about 0.035 Mpa. The recovery process was stopped when the concentration of recovered ethanol was lower than 40%.

2. Concentration

After the ethanol recovering, the liquid extract was transferred to a triple concentrator, which was composed by 3 serially-connected vacuum concentrators, according to the standard operating procedures for simultaneous concentration (3 chambers running at the same time). During concentration, the pressure of the vapor used for heating up the extract in the concentrator was maintained at 0.1~0.2 Mpa, the first chamber was at a vacuum of −0.03~−0.04 Mpa and the temperature of 80~85° C., the second chamber −0.05~0.06 Mpa and 65~70° C.; the third chamber −0.07~0.08 Mpa and 50~55° C. After the volumes of the extract in the first and second chambers were reduced, the concentrates were transferred to the third chamber to continue the concentration process. When the relative density of the concentrate in the third chamber reached around 1.05~1.12 (measured at 60±5° C.), preferably around 1.05~1.08, the concentration process was discontinued and the concentrate was collected for later use.

Spray Drying to Produce F2

The concentrate was heated up to a temperature of about 65° C. and was injected into the cabinet of a spray dryer by centrifugal spraying (no dextrin was added). The temperatures of the inlet and outlet air of the cabinet were adjusted to around 215° C. and around 90° C., respectively. The temperature of the inlet air had an impact on the yield of the total polysaccharides in the final powder products and the appearance of final powder products. At 160° C., 200° C. and 240° C. of incoming temperatures, the yield of total polysaccharides in the final Yunzhi powder products were 20.6%, 16.3% and 12.1%, respectively. The Yunzhi powder had a slightly bitter taste. The powder appeared dark brown at 160° C. or 200° C., and brown at 240° C., of the incoming air temperature.

The concentrate became dried powder in the cabinet. The powder was passed through a mill with an 80 mesh sieve. The fine powder, F2, was collected.

Outer Package

The powder (F2) was packed and sealed in aluminum foil bags by a vacuum packaging machine (3 Kg per bag). Each bag was packed with a second layer of aluminum foil and labeled appropriately after products from each batch were proved to conform to all tests. Bags were then placed in barrels and stored under cool, dry conditions.

Vacuum Drying to produce F2a

To produce F2a, the concentrate was mixed with Dextrin in mixer for 25 minutes. The mixture was then placed on cleaned trays of the vacuum drier and the mixture was dried at 70° C., vacuum pressure <−0.08Mpa. The drying process was stopped when the water content of the mixture is equal or less than 6%. The mixture was crushed and was passed through a mill with an 80 mesh sieve. The fine powder (F2a) was collected. The major components of the resulting Yunzhi powder extract F2a were found to be polysaccharides and triterpenoids.

High Performance Liquid Chromatography Studies

The present invention uses High performance Liquid Chromatograph (HPLC) to fingerprint Yunzhi powder products made by different drying methods.

The differences between F2 and F2a were detected by chemical profiling using a High performance Liquid Chromatography (HPLC) system, which separates chemical components according to differences in molecular size. The HPLC method and the test results are described as follows:

1. Materials and Methods 1.1 Sample Preparation for HPLC Analysis

F2 or F2a (84 mg) in powder form were separately dissolved in 1 ml of sterile double-distilled and deionized water with shaking at 100 rpm in a round bottom polypropylene microtube for over 12 hours. The solution of each was filtered through a 0.45 μm nylon acrodisc® syringe filter (Pall Corporation, N.Y., USA, catalog no. 4484) and stored at 4° C.

1.2 Molecular Size Standards

Molecular size standards containing a mixture of dextrans with molecular weights of 1,010 (Fluka, Buchs, Schweiz, catalog no. 31416) and 80,900 (Fluka, Buchs, Schweiz, catalog no. 31421), at 50 mg/ml each, were used as size markers to verify the consistency in performance of the HPLC system.

1.3 HPLC System

The entire HPLC system and all its mechanical parts were purchased from Waters Corporation, Mass., USA. The instruments used include Waters Alliance 2695 Separation Module, Waters 2410 Refractive Index Detector (R.I.), Waters 996 Photodiode Array Detector (Samples analyzed at UV 265 nm). Columns were: in serial connection as follows: 1. Ultrahydrogel Guard Column (catalog no. 11565); 2. Ultrahydrogel 1000 (catalog no. WAT011535); 3. Ultrahydrogel 500 (catalog no. WAT011530); and 4. Ultrahydrogel 250 (catalog no. WAT011525). The ultrahydrogel guard column was 6.0 mm in inner diameter and 40 mm in length. The ultrahydrogel analytical columns were all 7.8 mm in inner diameter and 300 mm in length.

1.4 HPLC Running Conditions

| Mobile phase: | Double distilled and deionized water (DDI) filtered through 0.45 μm nylon membrane filter |
| --- | --- |
| Washing solution: | Acetonitrile (ACN) filtered through 0.45 μm nylon membrane filter |
| Flow rate: | 0.3 ml/min |
| Sample run time: | 300 min for sample |
| | 120 min for the dextran standard |
| Sample injection volume: | 100 μl for sample |
| | 20 μl for dextran standard mixture |
| Purge detector: | 10 min (before injection of each sample or dextran standard mixture) |

Washing steps after each running of sample:

| | Duration | Flow rate (ml/min) | Condition |
| --- | --- | --- | --- |
| 1. | 10 min | 0.5 | 100% DDI |
| 2. | 30 min | 0.3 | gradual change from 100% DDI to 80% DDI + 20% ACN |
| 3. | 60 min | 0.3 | 80% DDI + 20% ACN |
| 4. | 30 min | 0.3 | gradual change from 80% DDI + 20% ACN to 100% DDI |
| 5. | 10 min | change from 0.3 to 0.5 | 100% DDI |
| 6. | 110 min | 0.5 | 100% DDI |

Washing after each running of size standard: 120 min with DDI at 0.3 ml/min.

Sample-Standard running order: The dextran standard mixture was run once at the beginning, in between and after the samples.

1.5 Analysis of Chemical Fingerprints of F2 and F2a

Chromatograms produced from different sample batches using either detection method (R.I. or UV 265 nm) were aligned and compared. Chromatograms produced from different batches of dextran standard mixtures using R.I. detection were also aligned and compared for verification of variations between the runs.

2. Results

Figure 2:
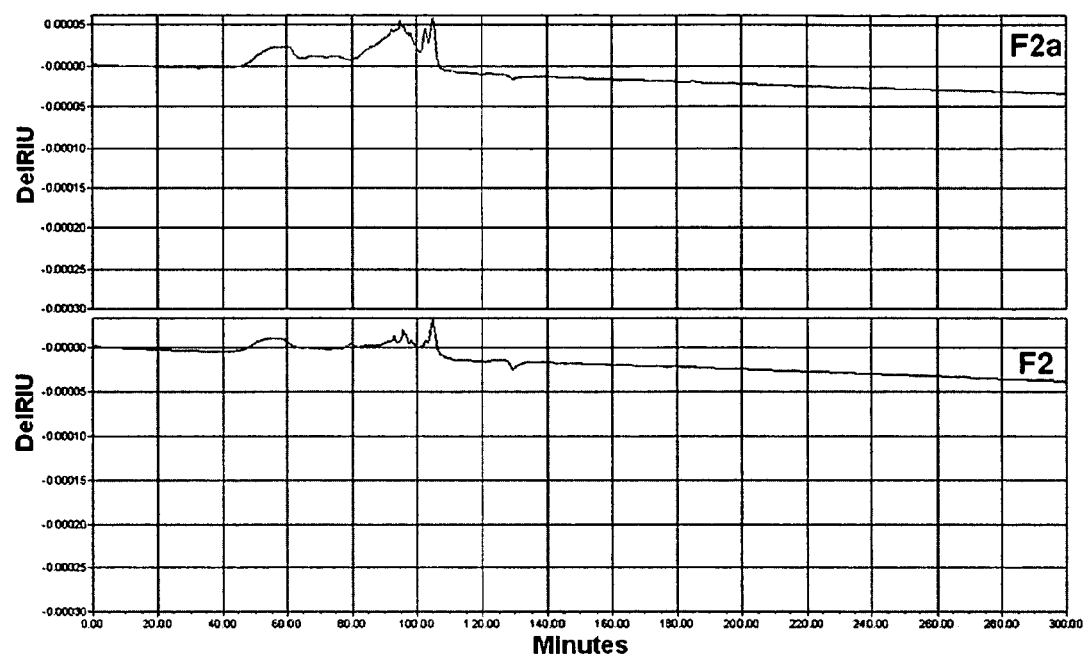
FIG. 2 shows the HPLC (high performance liquid chromatography) profiles of Yunzhi powder extracts F2a and F2 detected by refractive index (R.I.).
Figure 3:
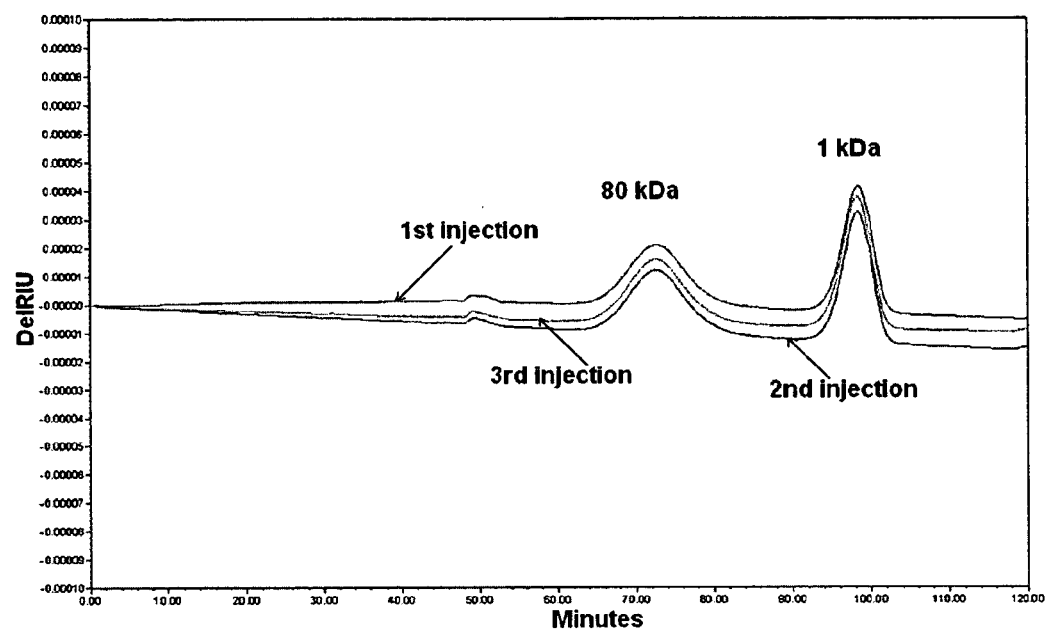
FIG. 3 shows the HPLC (high performance liquid chromatography) profiles of dextran standards in stacking chromatogram detected by refractive index (R.I.).

The HPLC based analysis of F2a and F2 samples produced more than seven discrete peaks using UV 265 nm detection, as shown in FIG. 1. The chromatograms for the two samples were similar except the difference in the intensity of three peaks (A, B, and C). The difference in the peak B intensity is significant because the relative intensity of this peak towards others in the same sample was different between F2a and F2. Detection with differential R.I. produced very similar patterns between the two samples and thus is not suitable for differential between them, as shown in FIG. 2. The test was verified by the alignment of chromatograms of the dextran standard mixtures and no significant variation in performance was detected, as shown in FIG. 3.

Pharmacological Studies

The following pharmacological studies demonstrated that Yunzhi derived formula F2 showed in vitro anti-proliferative activities in leukemia and breast cancer cell lines. And F2 was better than Yunzhi pure water extract for its selective cytotoxicity towards the cancer cells but not the normal human cell line. Such formulation could be potentially useful for treating patients with leukemia or breast carcinoma.

Although Yunzhi derived formulae F2 and F2a both demonstrated effectiveness in leukemia and breast cancer cell lines, F2 appeared to be superior to F2a in terms of the concentration required to produce 50% growth inhibition (IC50) for tumor cell lines, as determined by MTT assay. Although the IC50 value for Yunzhi pure water extract is smaller than that of F2 in both cases with the human cancer cell lines, the extract also showed very high cytotoxicity and small IC50 value with the normal human cell line. Therefore, the Yunzhi pure water extract did not possess the selective cytotoxicity as did F2, which demonstrated significant cytotoxicity towards the selected cancer cell lines but not the normal cell line. Therefore, we concluded that F2 is a better anticancer drug candidate than Yunzhi pure water extract.

Protocols of Cell Cultures and MTT Assay for Investigation of F2 and F2a

Cell Cultures

Prior to cell cultures, F2, F2a and Yunzhi pure water extract were dissolved in plain RPMI medium 1640 (Invitrogen GIBCO, NY, U.S.A.) as the stock solutions of 3.0 mg/ml, 2.2 mg/ml and 1.15 mg/ml respectively (due to different extent in solubility), for 48 h at room temperature with continuous shaking. Insoluble material was removed by centrifugation and the soluble supernatant was sterilized using a 0.22 μm filter, and further diluted with plain culture medium. For F2 and F2a, the concentration range after dilution was 25-1600 μg/ml (2× final concentration) while for Yunzhi pure water extract, the concentration was 1142.86 ug/ml (for final 800 μg/ml dosage) and a range of 25-800 μg/ml (2× final concentration).

Human acute promyelocytic leukemia (HL-60), breast carcinoma (MCF-7) and normal liver (WRL-68) cell lines were purchased from American Type Culture Collection (ATCC, MD, U.S.A.). The cell lines were grown and maintained in a humidified incubator at 37° C. and in 5% $CO_2$ atmosphere. RPMI medium 1640 supplemented with 20% fetal bovine serum (FBS), 100 units/ml penicillin, and 100 μg/ml streptomycin (Invitrogen GIBCO) were used for cell cultures of HL-60. RPMI medium supplemented with 10% FBS, 100 units/ml penicillin, and 100 μg/ml streptomycin were used as the culture medium of MCF-7 and WRL-68 cells.

After being harvested from culture flasks, the cells were counted using a hemocytometer and cell viability was determined by trypan blue exclusion. For assay with F2 and F2a, $10^4$ cells of the HL-60 cell line from log phase cultures were seeded in 100 μl of RPMI medium supplemented with 40% FBS per well of 96-well flat-bottom Costar culture plates (Corning Inc., MA, U.S.A.); while for MCF-7 cells, 5000 cells were seeded per well in 100 μl of RPMI medium supplemented with 20% FBS. One hundred microliters of solutions containing twice the final concentrations of F2 or F2a in plain culture medium were added per well. Control wells were added with 100 μl of plain medium alone. A chemotherapeutic antitumour drug, mitomycin C (MMC, Sigma Chemical Co., MO, U.S.A.) at a final concentration of 20 μg/ml was added as the positive control. For assay with Yunzhi pure water extract, $10^4$ cells of the HL-60 cell line were seeded in 60 μl of RPMI medium supplemented with 66.7% FBS per well; while 5000 cells of either the MCF-7 or WRL-68 cell lines were seeded per well in 60 μl of RPMI medium supplemented with 33.3% FBS. For dosage at 800 μg/ml, 140 μl of the diluted extract at 1142.86 ug/ml in plain culture medium were added per well. For dosage at 12.5-400 μg/ml, 100 μl of the diluted extract containing twice the final concentrations in plain culture medium were added per well. Control wells were added with 140 μl of plain medium alone. Cells were then incubated with the drugs for 48 h (MCF-7) or 72 h (HL-60). Proliferative responses of the treated cells were determined using MTT assay.

MTT Cytotoxicity Assay

MTT assay detects the reduction of MTT [3-(4,5-dimethylthiazolyl)-2,5-diphenyl-tetrazolium bromide, Sigma] by mitochondrial dehydrogenase to a blue formazan product, which reflects normally functioning of mitochondria and hence viable cells. Following incubation of cells with F2, F2a or Yunzhi pure water extract for 48 h (MCF-7 or WRL-68) or 72 h (HL-60), 30 μl of 5 mg/ml MTT in phosphate buffered saline (PBS, Invitrogen GIBCO) was added to each well and the plate was incubated at 37° C. for 2 h. The plate was then centrifuged and followed by removal of supernatant. One hundred microliter of dimethylsulfoxide (DM50, Sigma) was then added to each well. After incubation at 37° C. for 5 min, absorbance of the dissolved solution was detected spectrophotometrically at 540 nm by a Benchmark microtiter plate reader (Bio-Rad Laboratories, Calif, U.S.A.). The absorbance of untreated cells was considered as 100%. Results were expressed as the mean % of MTT absorbance (ratio of absorbance in Yunzhi powder extract-treated to that of control wells*100%)±standard deviation of 3 independent experiments with 6 wells each. Differences between the treated and untreated control (100%) wells were determined by Student's unpaired t-test.

MTT Assay Results for Comparison of in vitro Anti-tumor Activities of F2 and F2a on Human Promyelocytic Leukemia (HL-60) and Breast Carcinoma (MCF-7)

Figure 4:
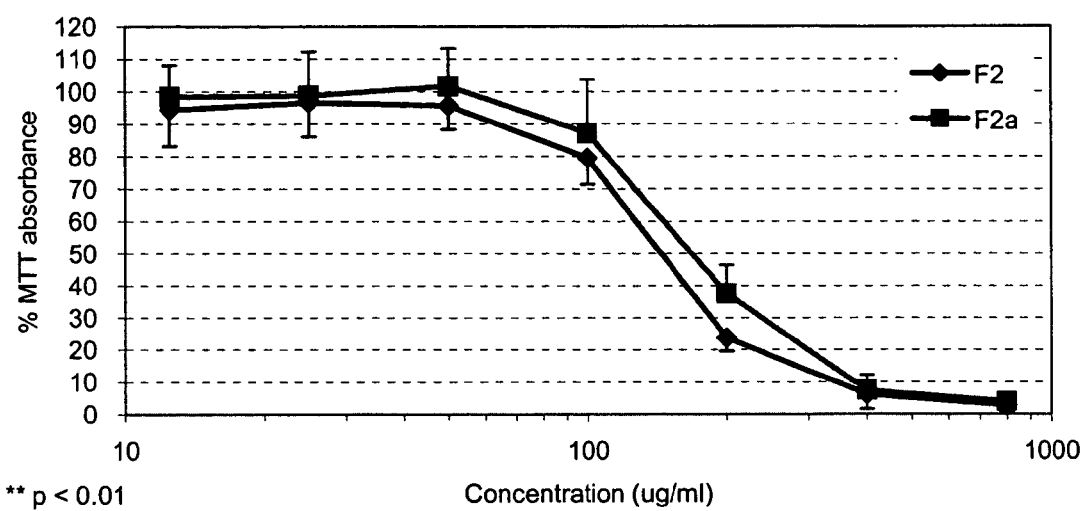
FIG. 4 shows anti-proliferative effect of F2 and F2a on HL-60 cells for 72 h at varying concentrations (n=6 wells, triplicate experiments).
Figure 5:
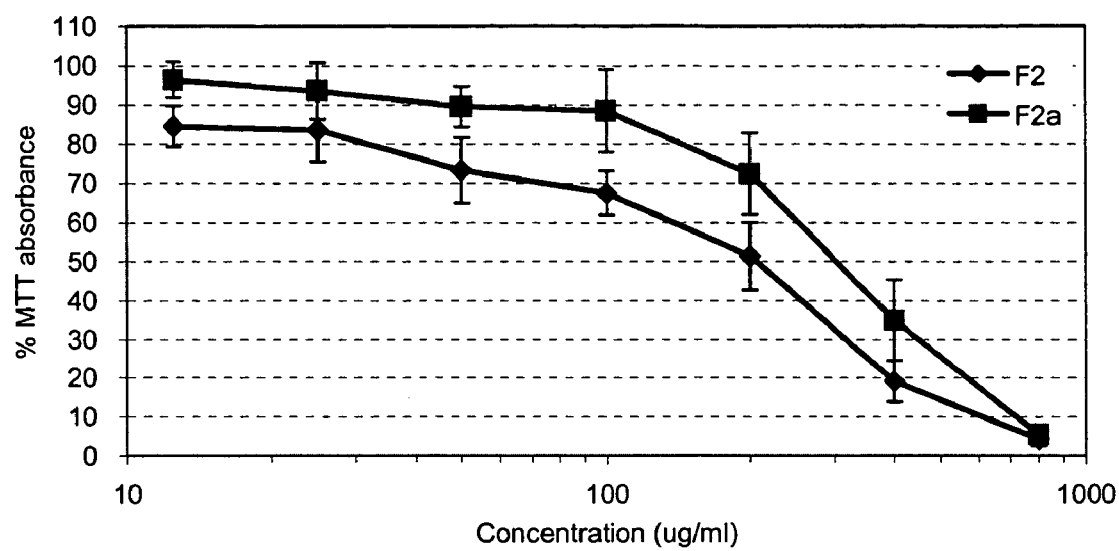
FIG. 5 shows anti-proliferative effect of F2 and F2a on MCF-7 cells for 48 h at varying concentrations (n=6 wells, triplicate experiments)

FIGS. 4 and 5 show both Yunzhi derived formulae, F2 and F2a, had in vitro anti-proliferative effects on human promyelocytic leukemia (HL-60) and breast carcinoma (MCF-7), respectively. Cells were incubated with increasing concentrations (12.5~800 μg/ml with 2-fold increase) of the Yunzhi powder extract in culture medium for 48 hours (MCF-7 cells) or 72 hours (HL-60 cells), and the proliferative response was assessed by MTT assay. Both Yunzhi powder extracts, F2 and F2a, could significantly inhibit the proliferation of MCF-7 cells (at 50 to 800 μg/ml) and HL-60 cells (at 100~800 μg/ml) in a dose-dependent manner.

These pharmacological studies proved that F2 had a lower $IC_{50}$ value and thus, was more active than F2a. Therefore, the Yunzhi derived formula of the present invention proved to be a better formulation than that manufactured by other process.

TABLE 1

| | $IC_{50}$ (μg/ml) | |
|---|---|---|
| | HL-60 | MCF-7 |
| F2 | 150.62 ± 5.65 | 235.45 ± 41.23 |
| F2a | 181.61 ± 10.29 | 323.41 ± 60.39 |
| p-value (Student's t-test) | 0.0102* | 0.1056 |

The "*" denotes the data is significant.

Figure 6:
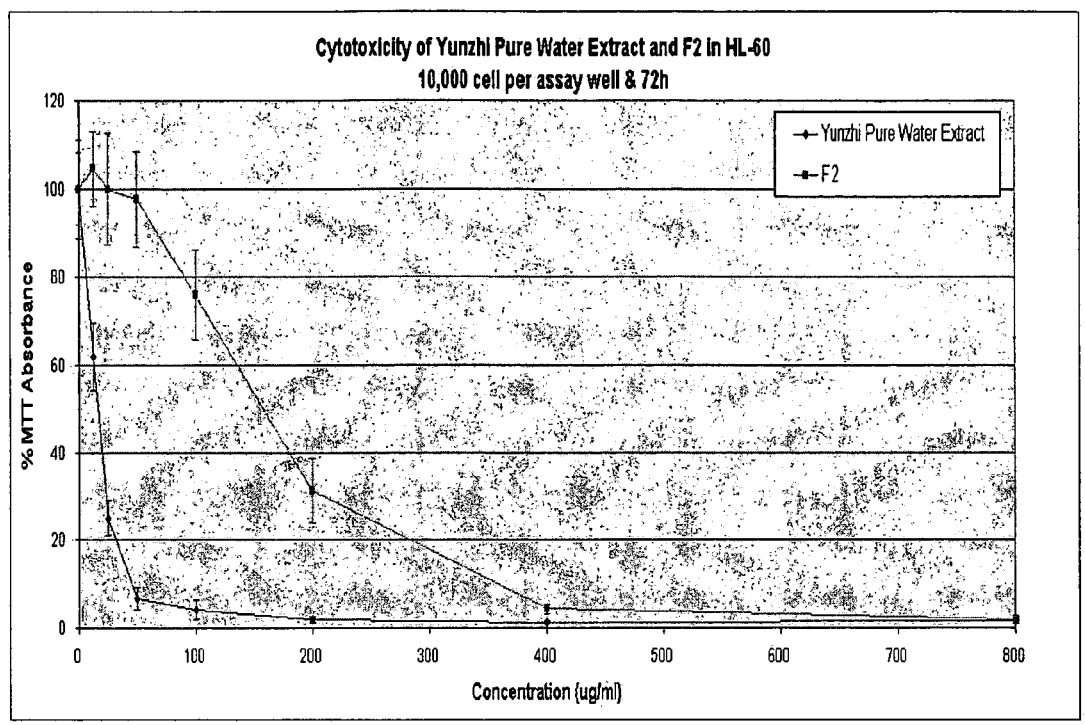
FIG. 6 shows the cytotoxicity of the water extract of Yunzhi and F2 in HL-60
Figure 7:
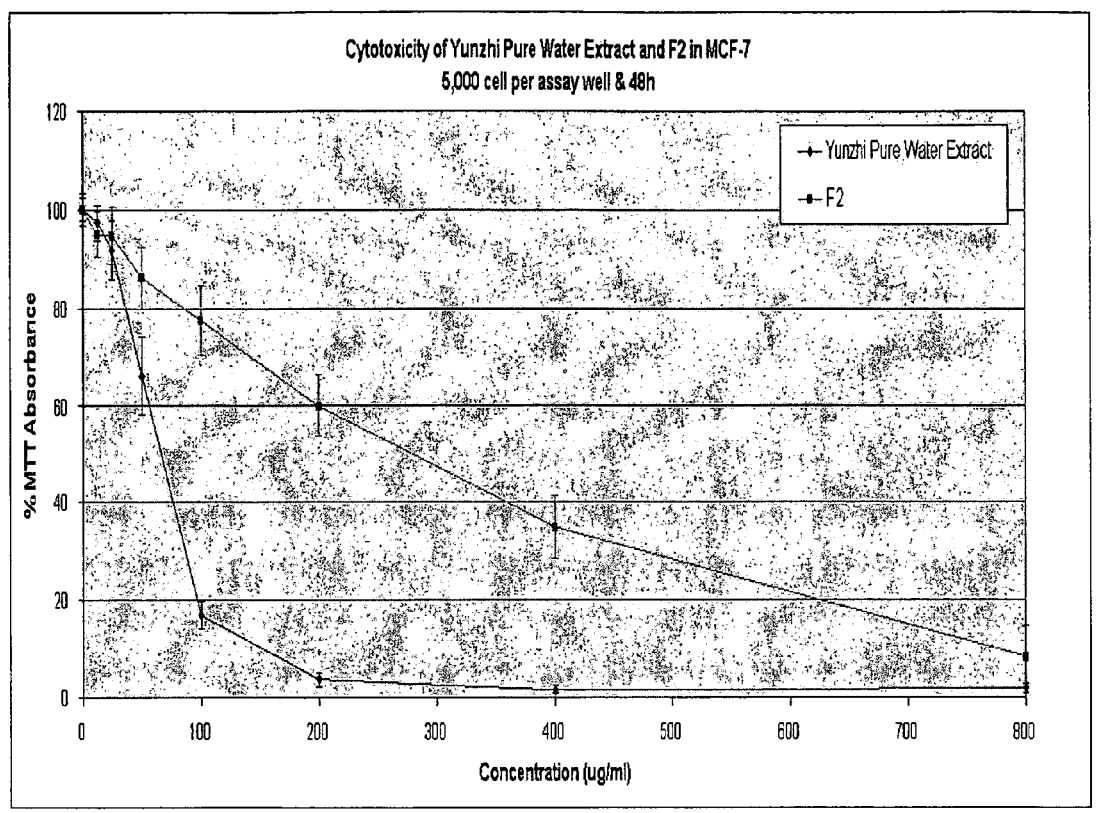
FIG. 7 shows the cytotoxicity of the water extract of Yunzhi and F2 in MCF-7
Figure 8:
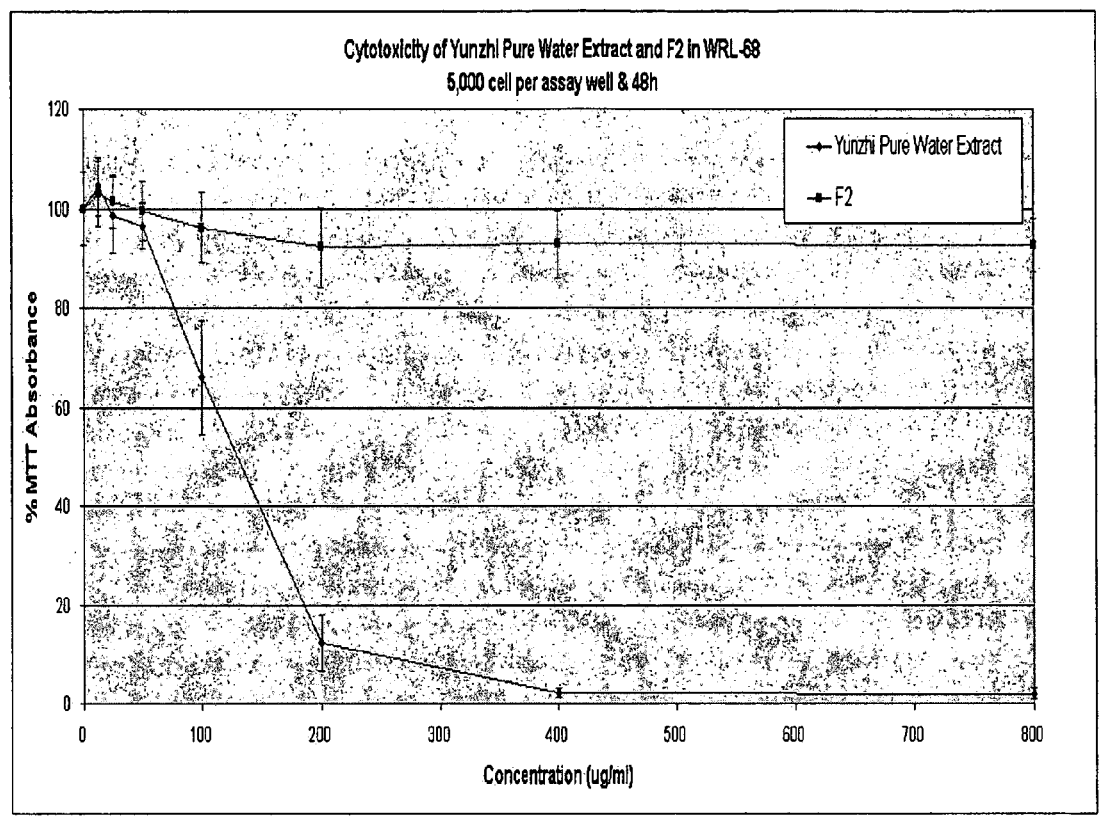
FIG. 8 shows the cytotoxicity of the water extract of Yunzhi and F2 in WRL-68

FIGS. 6, 7 and 8 show the results of in vitro anti-proliferative effects of Yunzhi derived formulae, F2 and Yunzhi pure water extracts, on human promyelocytic leukemia (HL-60), breast carcinoma (MCF-7) and normal liver cells (WRL-68), respectively. Cells were incubated with increasing concentrations (12.5~800 μg/ml with 2-fold increase) of the Yunzhi derived formulae in culture medium for 48 hours (MCF-7 or WRL-68 cells) or 72 hours (HL-60 cells), and the proliferative response was assessed by MTT assay. Both Yunzhi derived formulae, F2 and Yunzhi pure water extract, could significantly inhibit the proliferation of MCF-7 cells (at 50 to 800 μg/ml) and HL-60 cells (at 100~800 μg/ml) in a does-dependent manner. However, only the Yunzhi pure water extract demonstrated significant inhibition of the proliferation of WRL-68 cells (at 100 to 800 μg/ml) while the F2 did not show any significant inhibition throughout the tested concentration range (12.5 to 800 μg/ml).

Table 2 shows the $IC_{50}$ values of the Yunzhi derived formulae F2 and Yunzhi pure water extract on the tested cell lines. Proliferation of MCF-7 cells was significantly inhibited by F2 and Yunzhi pure water extract starting at 50 μg/ml with $IC_{50}$ values at 235.45±41.23 µg/ml and 59.39±5.92 µg/ml, respectively. Proliferation of HL-60 cells was significantly inhibited by F2 and Yunzhi pure water extract starting at 100 µg/ml with $IC_{50}$ values at 150.62±5.65 µg/ml and 14.85±1.18 µg/ml, respectively. Proliferation of WRL-68 cells was significantly inhibited by Yunzhi pure water extract starting at 100 µg/ml with $IC_{50}$ values at 127.91±17.85 µg/ml. There was no significant inhibition of the proliferation of WRL-68 cells by F2 throughout the tested concentration range from 12.5 to 800 µg/ml.

The result clearly indicated that although the IC50 value for Yunzhi pure water extract is smaller than that of F2 in both cases with human cancer cell line HL-60 and MCF-7, the extract also showed very high cytotoxicity and small IC50 value with the normal human cell line WRL-68. Therefore, the Yunzhi pure water extract did not possess the selective cytotoxicity as did F2, which demonstrated significant cytotoxicity towards the selected cancer cell lines but not the normal cell line. Therefore, These pharmacological studies proved that present invention proved to be a better anticancer drug candidate than Yunzhi pure water extract.

TABLE 2

| | $IC_{50}$ (µg/ml) | | |
| --- | --- | --- | --- |
| | HL-60 | MCF-7 | WRL-68 |
| F2 | 150.62 ± 5.65 | 235.45 ± 41.23 | >800 |
| Yunzhi pure water extract | 14.85 ± 1.18 | 59.39 ± 5.92 | 127.91 ± 17.85 |
| p-value (Student's t-test) | <0.001* | 0.029* | <0.001* |

The "*" denotes the data is significant.

We claim:

1. A *Coriolus versicolor* (Yunzhi) extract powder wherein said Yunzhi extract powder is obtained by:
   a. extracting Yunzhi coarse powder with an alcoholic solvent to obtain a liquid extract;
   b. filtering said liquid extract obtained in step (a) to obtain a filtrate;
   c. concentrating said filtrate obtained in step (b) to obtain a concentrated filtrate; and
   d. spray-drying said concentrated filtrate obtained in step (c) to obtain said Yunzhi extract powder
   wherein said Yunzhi extract powder has a IC50 value of less than 160 ug/ml for the cell line HL-60.

2. The extract powder according to claim 1, wherein said Yunzhi extract has a high performance liquid chromatography fingerprint of F2 as shown in FIG. 1.

3. The extract powder according to claim 2, wherein said extract step (a) is performed two times with 50% ethanol:50% water (v/v) followed by extracting two times with water.

4. The extract powder according to claim 2, wherein said extract powder is capable of stimulating or modulating an immune system, treating hepatitis, or inhibiting growth of cancer cells in a human or other mammal.

5. The extract powder according to claim 2, where the extract powder is capable of inhibiting growth of leukemia or breast carcinoma cells in a human or other mammal.

6. The extract powder according to claim 2, wherein said extract powder is formulated as one selected from the group consisting of granule, a capsule, a tablet, a powder and a bolus.

7. The extract powder according to claim 6, wherein said extract powder is in the form of a capsule.

\* \* \* \* \*